United States Patent

Häkkinen

[11] 4,328,796
[45] May 11, 1982

[54] RESPIRATION PACEMAKING VALVE FOR RESUSCITATION APPARATUS SUCH AS RESPIRATORS

[76] Inventor: Taisto Häkkinen, Kaarlonkatu 25, 13210 Häeenlinna 21, Finland

[21] Appl. No.: 109,433

[22] Filed: Jan. 3, 1980

[30] Foreign Application Priority Data

May 1, 1979 [FI] Finland .................. 790038

[51] Int. Cl.³ .......................................... A61M 11/02
[52] U.S. Cl. ...................... 128/200.14; 128/200.21; 128/203.13; 128/204.25; 128/205.24
[58] Field of Search ............ 128/200.18, 200.21, 128/203.25, 204.25, 204.18, 204.19, 200.14, 205.11, 203.12, 203.13, 205.24

[56] References Cited

U.S. PATENT DOCUMENTS

| | | | |
|---|---|---|---|
| 2,181,421 | 11/1939 | Fahr et al. | 128/200.21 |
| 3,057,349 | 10/1962 | Ismach | 128/207.23 |
| 3,301,255 | 1/1967 | Thompson | 128/200.18 |
| 3,581,742 | 6/1971 | Glenn | 128/204.19 |
| 3,717,147 | 2/1973 | Flynn | 128/204.25 |
| 4,202,330 | 5/1980 | Jariabka | 128/205.24 X |

FOREIGN PATENT DOCUMENTS

| | | | |
|---|---|---|---|
| 978278 | 4/1951 | France | 128/205.24 |
| 2019223 | 10/1979 | United Kingdom | 128/200.21 |

*Primary Examiner*—Henry J. Recla
*Attorney, Agent, or Firm*—Steinberg and Raskin

[57] ABSTRACT

Respiration pacemaking valve apparatus adapted for use with apparatus for resuscitation such, for example, as a respirator, including a body member or housing defining a fluid flow passage, an inlet through which air or oxygen can be conducted into the fluid flow passage and wherein the body member is attached directly to a drug atomizer in a manner such that air or oxygen can be further conducted to the regulating valve assembly of a respirator or an outgoing connecting branch of other resuscitation apparatus. A spindle is disposed within the fluid flow passage of the body member which is provided with an elastic portion for opening and closing the fluid flow passage thereof in response to actuation of a trigger member pivotally mounted on the body member.

5 Claims, 4 Drawing Figures

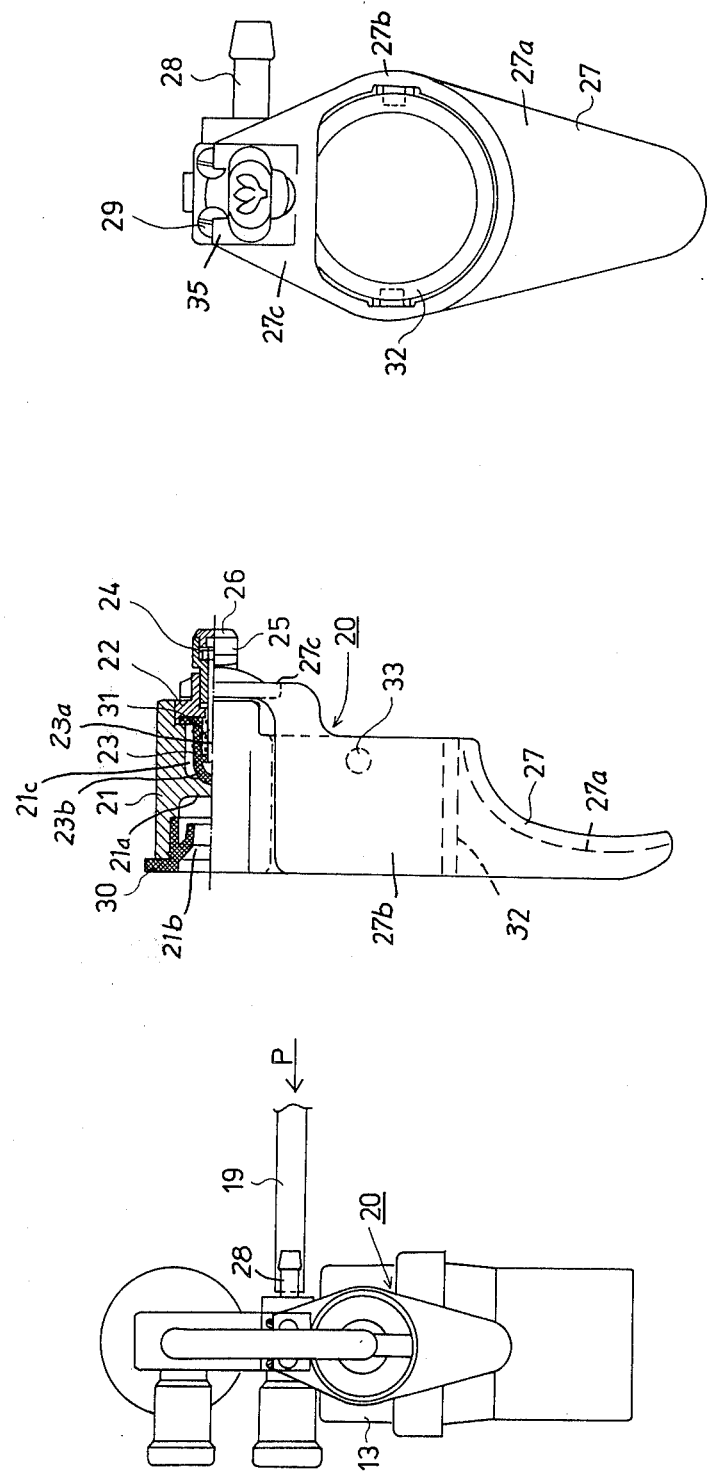

RESPIRATION PACEMAKING VALVE FOR RESUSCITATION APPARATUS SUCH AS RESPIRATORS

BACKGROUND OF THE INVENTION

This invention relates generally to resuscitation apparatus and, more particularly, to a respiration pacemaking valve adapted to be mounted on resuscitation apparatus such, for example, as respirators.

Resuscitation apparatus which operate in conjunction with respiration pacemaking valves are known. For example, a respirator is disclosed in Finnish Pat. No. 53927 which is connected to a source of compressed air or oxygen, such as a compressor or equivalent compressed air generating means, an oxygen flask or other oxygen supply system. The respirator comprises a distributor member having a branch passage which is mediated by a first flexible tube through which the compressed air or oxygen is conducted to a second flexible tube which directs the air or oxygen to a drug atomizer. During the inspiration phase of operation, the drug dispensed from the drug atomizer is admixed with the respiration air flowing from the injector into a mouthpiece in the form of minute droplets. A respiration pacemaking valve is provided between the distributor member and a filter housing, the latter serving both as a filter and as the hand grip of the respirator. This arrangement of the respiration pacemaking valve and associated respirator is the same in other resuscitation apparatus and respirators currently in use.

However, the particular arrangement of the respiration pacemaking valve and resuscitation as described above is not entirely satisfactory in that a complex regulating valve assembly including various branches and connectors is required in order to direct the flow of compressed air or oxygen in the respirator in view of the provision of the pacmaking valve. As a result thereof, conventional respirators and other resuscitation apparatus are generally both bulky and complex in construction and therefore expensive in manufacture.

Another type of respirator is known which does not include a respiration pacemaking valve. More particularly, a respirator is disclosed in Finnish Patent Application No. 78 1170 wherein the flow of air or oxygen into the drug atomizer during the patient's expiration can be prevented by squeezing a pressure tube which is provided with a loop therein. A sleeve fits over the loop of the pressure tube which is adapted to slide thereover to selectively adjust the gas flow therethrough so that the latter can be increased, decreased or entirely obstructed as desired. From the above, it is seen that the looped pressure tube and associated sliding sleeve does not in fact function as a respiration pacemaking valve but, rather, serves as a regulating means for the gas flow.

SUMMARY OF THE INVENTION

Accordingly, one object of the present invention is to provide new and improved resuscitation apparatus, such as a respirator, equipped with a respiration pacemaking valve.

Another object of the present invention is to provide a new and improved respiration pacemaking valve which can be rapidly and easily attached to resuscitation apparatus, such as a respirator.

Still another object of the present invention is to provide a new and improved respiration pacemaking valve which has a maximum reliability during operation.

Yet another object of the present invention is to provide a new and improved respiration pacemaking valve of simple construction and which can be associated with conventional resuscitation apparatus, such as respirators, without the need for structural alterations therein.

Briefly, in accordance with the present invention, these and other objects are attained by providing a respiration pacemaking valve adapted to be connected directly to the drug atomizer so that the air or oxygen is conducted into the body member of the pacemaking valve or into the housing thereof and whereupon the air or oxygen is then carried in the case of a respirator to the regulating valve or in the case of other resuscitation apparatus to the appropriate outgoing connecting branch of the apparatus.

Numerous significant advantages are obtained by the present invention. For example, the respiration pacemaking valve can be rapidly and easily attached to a respirator or other resuscitation apparatus. No structural changes or additional equipment are required in order to effect the connection of the respiration pacemaking valve to the apparatus. By virtue of the simplified construction thereof, the respiration pacemaking valve of the present invention is more reliable in operation and simpler in construction than pacemaking valves and associated resuscitation apparatus of the prior art.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which:

FIG. 2 is a rear elevation view of the apparatus illustrated in FIG. 1;

FIG. 3 is a side elevation view in partial section of a respiration pacemaking valve according to the present invention; and FIG. 4 is a rear elevation view of the respiration pacemaking valve illustrated in FIG. 3.

DESCRIPTION OF THE PREFERRED EMBODIMENT

Figure 1:
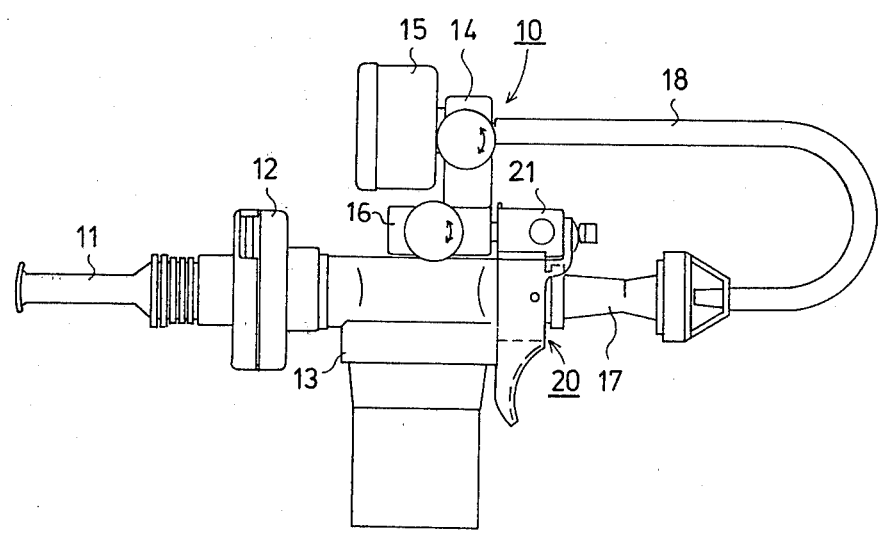
FIG. 1 is a side elevation view of a respirator incorporating a respiration pacemaking valve according to the present invention.

Referring now to the drawings wherein like reference characters designate identical or corresponding parts throughout the several views and more particularly to FIGS. 1 and 2, a conventional respirator, generally designated 10, is illustrated in conjunction with an associated respiration pacemaking valve, generally designated 20, according to the present invention. The respirator 10 may, for example, comprise the respirator disclosed in Finnish Patent Application No. 78 1170. Thus, the respirator 10 includes a mouthpiece 11, a drug atomizer 13 and a regulating valve 14. A valve 12 is preferably inserted between the mouthpiece 11 and the drug atomizer 13 by which the counter-pressure acting in opposition to the expiration flow can be adjusted in a continuous manner. One type of such valve is disclosed in Finnish Patent Application No. 78 1171. The respiration pressure is controlled by the regulating valve 14 and to this end, the valve 14 is provided with a pressure gauge 15. Respirator 10 further comprises a regulating valve 16 which forms part of the drug atomizer 13 by the aid of which the flow of air of oxygen through the drug atomizer can be regulated. Finally, the respirator 10 includes an injector 17 which is interconnected to the regulating valve 14 by means of flexible tubing 18.

According to the present invention, the respiration pacemaking valve 20 is directly connected to the drug atomizer 13 in a manner such that the air or oxygen is conducted into the pacemaking valve 20. The pacemaking valve 20 includes a body member 21 which functions as a pressure valve as described below and which is provided with a conventional connector 28 to which one end of the input tube 19 is connected whereby the pressurized air or oxygen is directed into the body member 21 of the pacemaking valve 20. The pressure, designated P, is carried from the pressure valve or body member 21 to the regulating valve assembly comprising the regulating valves 14, 16.

Turning now to FIGS. 3 and 4, a particularly advantageous construction of the respiration pacemaking valve 20 is illustrated. In this embodiment, the pacemaking valve 20 comprises body portion 21 which constitutes the housing for the respiration pacemaking valve 20. The body member 21 in the preferred embodiment has a transversely extending wall 21a which divides its interior into forward and rearward chambers 21b, 21c, respectively. The pacemaking valve 20 further comprises a cover member 22 and a trigger member 27 described in detail below.

A spindle 23 is disposed within the rearward chamber 21c of body member or housing 21 and has its rearward end secured, such as by hex nut 24 to a knob 25 which as seen in FIG. 3 has an elongate portion slidably received in cover member 22. A plate 26 covers the hex nut 24. The body member or housing 21 of the pacemaking valve 20 is further provided with a hose connector 28 to which the input tube 19 is connected for conducting air or oxygen into the rearward chamber 21c of body member or housing 21. The cover member 22 is fixedly secured to body member 21 by conventional means, such as by screws 29 (FIG. 4). A shaped rubber connector seal 30 (FIG. 3) is provided over the forward region of the forward chamber 21b of body member of housing 21 in order to provide a positive sealing between the body member 21 and the regulating valve assembly comprising valves 14, 16.

A substantially cylindrical mounting sleeve 32 is preferably integrally formed with the body member or housing 21 below the same. The trigger member 27 has a lower portion 27a adapted to be engaged by the finger of an operator, an intermediate cylindrical portion 27b having a generally cylindrical configuration in whose interior the mounting sleeve 32 is received and an upper portion 27c which is operatively connected to the spindle 23 in a manner described below. The trigger member 27 is pivotally attached to the body member or housing 21 by means of a pair of pivot pins 33 at the mediate portions of mounted sleeve 32 and intermediate cylindrical portion 27b of trigger member 27.

As best seen from FIG. 3, the spindle 23 comprises a rearwardly axial portion 23a, preferably formed of a metallic material, and a forward elastic portion 23b comprising the forward end of the spindle 23. The rear end of axial portion 23a is fixed to hex nut 24. A coil spring 31 is mounted over the axial portion 23a of spindle 23 and has ends which engage a transverse wall portion of spindle 23 and cover member 22, respectively. Spring 31 functions as a return spring for urging the spindle 23 to its normally closed position as described below. The spring 31 normally urges the elastic forward portion 23b of spindle 23 against the transverse wall 21a of the body member or housing 21 to close the passage provided therein so that in this manner, the pressurized air or oxygen admitted into the rearward chamber 21c of housing 21 is prevented from passing into the forward chamber 21b thereof and, accordingly, to the regulating valves 14, 16. As seen in FIG. 3, the forward elastic portion 23b of spindle 23 has an annular shoulder which abuts against the cover member 22. In other words, the spindle 23 in its normal position closes the valve and provides a reliable seal preventing the access of air or oxygen from the valve housing to the regulating valve assembly.

The upper portion 27c of trigger member 27 includes a bifurcated portion 35 which is disposed behind the knob 25 to which the hex nut 24 is secured at its rearward end. Thus, referring to FIGS. 3 and 4, the knob 25 extends through the space defined by the bifurcated portion 35. It will be readily appreciated that upon the operator urging the lower portion 27a of trigger member 2 towards the left as seen in FIG. 3, the upper portion 27c of the trigger member will act on the slidable knob 25 thereby urging the hex nut and elastic spindle portion 23b attached thereto through the axial spindle portion 23a towards the right as seen in FIG. 3 against the force of return spring 31. In this manner, the air or oxygen introduced through tube 19 into the body member of housing 21 is permitted to pass therethrough into the regulating valve assembly 14, 16. Upon release of the pressure on the lower portion of the trigger member 27, the return spring returns the spindle elastic portion to its closed position thereby precluding gas flow.

It should be noted that the purpose of the cover member 22 is to affix the elastic spindle portion with a positive sealing pressure to prevent any leakage of the pressurized gas from within the body member or housing 21 through the spindle 23 into the ambient atmosphere when the trigger member 27 is in its closed position.

Further, since the return spring 31 associated with spindle 23 is located within an enclosed volume and extends between the elastic and metallic portions of the spindle 23, any moisture present in the air or oxygen cannot oxidize and damage the return spring 31.

Obviously, numerous modifications and variations of the present invention are possible in the light of the above teachings. It is therefore to be understood that within the scope of the appended claims, the invention may be practiced otherwise than as specifically disclosed herein.

What is claimed is:

1. Respirator apparatus comprising:
   a drug atomizer;
   regulating valve means fluidly connected to said drug atomizer for controlling respiratory pressure and for controlling a flow of air or oxygen to said drug atomizer; and
   a respirator pacemaker valve directly connected to said drug atomizer and including a body member defining a fluid flow passage therein in fluid communication with said regulating valve means and having gas inlet means for receiving air or oxygen from a source thereof and directing the same into said fluid flow passage, a spindle member mounted within said fluid flow passage for movement between a first position wherein said fluid flow passage is closed to prevent fluid communication between said gas inlet and said regulating valve means and a second position wherein said fluid flow passage is open to allow said fluid communication, and a trigger member pivotally connected to said body member and operable through the application of finger pressure thereto for moving said spindle member between said open and closed positions, said trigger member having a portion coupled to said spindle member for movement thereof upon actuation of said trigger member.

2. Apparatus as recited in claim 1 wherein said spindle includes an elastic portion adapted to open and sealingly close said fluid flow passage.

3. Apparatus as recited in claim 2 wherein said spindle member includes an axial portion and an elastic portion provided at one end of said axial portion adapted to open and sealingly close said fluid flow passage and further including spring means located over said axial portion of said spindle member, said spring means normally urging said spindle member into said first closed position; a knob member having an elongate portion slidably mounted in said body member and a knob portion formed at an end of said elongate portion; the other end of said axial spindle portion being secured to said knob member; and wherein said trigger member is operatively connected to said knob portion so that upon pivoting said trigger member said knob member is slidably moved to move said spindle member against the force of said spring means from said first closed position to said second open position.

4. Apparatus as recited in claim 1 wherein said body member has an attachment sleeve integrally formed thereon and wherein said trigger member is pivotally attached to said sleeve.

5. Apparatus as recited in claim 1 further including a rubber-like connector seal affixed to one end of said fluid flow passage of said body member for tightly sealing said body member to said regulating valve assembly means.

* * * * *